US012678486B2

(12) United States Patent     (10) Patent No.:    US 12,678,486 B2
Rezvani et al.           (45) Date of Patent:       Jul. 14, 2026

(54) CELL IMMUNOTHERAPY FOR THE TREATMENT OF CANCER

(71) Applicant: BOARD OF REGENTS, THE UNIVERSITY OF TEXAS SYSTEM, Austin, TX (US)

(72) Inventors: Katy Rezvani, Houston, TX (US); Mayra Shanley, Houston, TX (US); David Marin Costa, Houston, TX (US); Hila Shaim, Houston, TX (US); Elizabeth Shpall, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 886 days.

(21) Appl. No.: 17/904,408

(22) PCT Filed: Mar. 25, 2021

(86) PCT No.: PCT/US2021/024123
§ 371 (c)(1),
(2) Date: Aug. 17, 2022

(87) PCT Pub. No.: WO2021/202232
PCT Pub. Date: Oct. 7, 2021

(65) Prior Publication Data
US 2023/0074303 A1     Mar. 9, 2023

Related U.S. Application Data

(60) Provisional application No. 63/001,275, filed on Mar. 28, 2020.

(51) Int. Cl.
| | |
|---|---|
| *A61K 38/20* | (2006.01) |
| *A61K 40/15* | (2025.01) |
| *A61K 40/42* | (2025.01) |
| *A61K 45/06* | (2006.01) |
| *A61P 35/00* | (2006.01) |
| *C07K 14/54* | (2006.01) |
| *C12N 5/0783* | (2010.01) |

(52) U.S. Cl.
CPC ............ *A61K 38/208* (2013.01); *A61K 38/20* (2013.01); *A61K 40/15* (2025.01); *A61K 40/4234* (2025.01); *A61K 45/06* (2013.01); *A61P 35/00* (2018.01); *C07K 14/54* (2013.01); *C07K 14/5434* (2013.01); *C12N 5/0646* (2013.01); *A61K 2239/31* (2023.05); *A61K 2239/38* (2023.05); *A61K 2239/47* (2023.05)

(58) Field of Classification Search
CPC .. A61K 38/20; A61K 38/208; A61K 38/2046; A61K 38/2013
See application file for complete search history.

(56) References Cited

U.S. PATENT DOCUMENTS

| | | |
|---|---|---|
| 2014/0255363 A1 | 9/2014 | Metelitsa et al. |
| 2018/0273903 A1 | 9/2018 | Zhang et al. |
| 2018/0333435 A1 | 11/2018 | Rezvani et al. |
| 2018/0353544 A1 | 12/2018 | Rezvani et al. |
| 2020/0085872 A1 | 3/2020 | Rezvani et al. |
| 2020/0113939 A1 | 4/2020 | Rezvani et al. |
| 2020/0390815 A1 | 12/2020 | Ang et al. |
| 2020/0390816 A1 | 12/2020 | Nassif et al. |
| 2021/0147800 A1 | 5/2021 | Rezvani et al. |
| 2021/0186877 A1 | 6/2021 | Shpall et al. |
| 2021/0230548 A1 | 7/2021 | Daher et al. |
| 2021/0393698 A1 | 12/2021 | Shpall et al. |
| 2022/0023343 A1 | 1/2022 | Rezvani et al. |
| 2022/0031749 A1 | 2/2022 | Basar et al. |
| 2022/0033778 A1 | 2/2022 | Shpall et al. |
| 2022/0033848 A1 | 2/2022 | Rezvani et al. |
| 2022/0175837 A1 | 6/2022 | Rezvani et al. |
| 2022/0288121 A1 | 9/2022 | Rezvani et al. |
| 2022/0325245 A1 | 10/2022 | Rezvani et al. |
| 2022/0370500 A1 | 11/2022 | Rezvani et al. |
| 2022/0378739 A1 | 12/2022 | Rezvani et al. |
| 2022/0389383 A1 | 12/2022 | Rezvani et al. |
| 2022/0401479 A1 | 12/2022 | Rezvani et al. |
| 2022/0403418 A1 | 12/2022 | Rezvani et al. |
| 2022/0409663 A1 | 12/2022 | Fix et al. |
| 2023/0040477 A1 | 2/2023 | Rezvani et al. |
| 2023/0045174 A1 | 2/2023 | Rezvani et al. |
| 2023/0060351 A1 | 3/2023 | Rezvani |
| 2023/0159618 A1 | 5/2023 | Ang et al. |

FOREIGN PATENT DOCUMENTS

| | | | |
|---|---|---|---|
| CN | 108060137 | 5/2018 | |
| CN | 110760480 A | 2/2020 | |
| WO | WO2013040371 A2 * | 3/2013 | .............. A61P 35/00 |
| WO | WO 2015/154012 | 10/2015 | |
| WO | WO 2016/201304 | 12/2016 | |
| WO | WO 2017/075537 | 5/2017 | |
| WO | WO 2019/141270 | 7/2019 | |
| WO | WO 2019/226708 | 11/2019 | |
| WO | WO 2020/028656 | 2/2020 | |
| WO | WO 2020/057641 | 3/2020 | |
| WO | WO 2021/101467 | 5/2021 | |

OTHER PUBLICATIONS

Kailyangiri et al. (2017), OncoImmunology, vol. 6, No. 1, e1250050 (15 pages) https://doi.org/10.1080/2162402X.2016.1250050.*
Bollino et al., Transl Res. Sep. 2017; 187:32-43. doi: 10.1016/j.trsl. 2017.06.003.*
Markley et al. Blood, 115(17):3508-3519 (Year: 2010).*
(Continued)

*Primary Examiner* — Prema M Mertz
(74) *Attorney, Agent, or Firm* — Norton Rose Fulbright US LLP

(57) ABSTRACT

Embodiments of the disclosure encompass compositions comprising immune effector cells, such as natural killer (NK) cells, where the cells comprise one or more exogenously provided interleukins (IL), and wherein the cell optionally comprises one or more engineered receptors. In specific embodiments, the IL is not IL-15, and is IL-12, IL-21, or both. The NK cells may be utilized for treatment of cancer of any kind, including at least glioblastoma.

6 Claims, 7 Drawing Sheets

(56) References Cited

OTHER PUBLICATIONS

Extended European Search Report for Application No. 21779007.0, mailed Nov. 8, 2024, 17 pages.

English translation of Office Communication issued in Japanese Patent Application No. 2022-558492, dated Mar. 12, 2025.

Luo et al, "Target-Dependent Expression of Il12 by synNotch Receptor-Engineered Nk92 Cells Increases the Antitumor Activities of CAR-T Cells," Frontiers in Oncology, 9, Article 1448, pp. 1-11, 2019.

Office Communication issued in European Patent Application No. 21779007.0, dated Jul. 19, 2024.

Chiocca et al., "Regulatable interleukin-12 gene therapy in patients with recurrent high-grade glioma: Results of a phase 1 trial," Sci. Transl. Med., 11:eaaw5680, 13 pages, 2019.

PCT International Search Report and Written Opinion issued in International Application No. PCT/US2021/024123, dated Jun. 23, 2021.

Hu et al., "Natural Killer Cell-Based Immunotherapy for Cancer: Advances and Prospects," Engineering, 5:106-114, 2019.

Office Communication issued in Singapore Patent Application No. 11202253530B dated Dec. 27, 2025.

Chaix et al., "Cutting Edge: Priming of NK Cells by Il-18," The Journal of Immunology, 181:1627-1631, 2008.

Coquet et al., "IL-21 is produced by NKT cells and modulates NKT cell activation and cytokine production," The Journal of Immunology, 178:2827-2834, 2007.

Lim et al., "Effect of exposure to interleukin-21 at various time points on human natural killer cell culture," Cryotherapy, 16:1419-1430, 2014.

Wang et al., "Human invariant natural killer T cells acquire transient innate Responsiveness via histone H4 acetylation induced by weak TCR stimulation," J. Exp. Med., 209(5):987-1000, 2012.

* cited by examiner

CELL IMMUNOTHERAPY FOR THE TREATMENT OF CANCER

This application is a national phase application under 35 U.S.C. § 371 that claims priority to International Application No. PCT/US2021/024123, filed Mar. 25, 2021, which claims priority to U.S. Provisional Patent Application Ser. No. 63/001,275, filed Mar. 28, 2020, each of which are incorporated by reference herein in their entirety.

TECHNICAL FIELD

Embodiments of the disclosure concern at least the fields of cell biology, molecular biology, immunology, and medicine.

BACKGROUND

Glioblastoma (GBM) is an aggressive malignancy with a poor prognosis. After recurrence, there is no standard therapy, and survival is less than 9 months. Results from three first-in-man chimeric antigen receptor (CAR) T-cell trials targeting IL13Rα2 (Brown et al., 2016), Her2/CMV (Ahmed et al., 2010), and EGFRvIII (O'Rourke et al., 2017) were recently reported with disappointing clinical results.

There is currently a critical need to advance cellular therapies against GBM, as well as other solid tumors, especially with the great responses they proved in leukemia and lymphoma. The present disclosure provides solutions to long-felt needs of advancing cellular therapy against cancers, including at least glioblastoma.

BRIEF SUMMARY

Embodiments of the disclosure include methods and compositions related to cell therapies for a medical condition. The cell therapies encompass immune effector cells or other cells for administration to an individual in need thereof. In specific embodiments, the cells are enhanced in activity compared to other cell therapies because the cells comprise one or more exogenously provided interleukins (IL) and optionally comprise one or more other heterologous gene products, such as one or more engineered receptors. The cells may be exposed externally to one or more cytokines (such as in culture) and/or they may be transfected to express a heterologous cytokine (as opposed to the endogenous cytokines expressed from the genome of the cell), including from one or more vectors. The disclosure encompasses immunotherapy with ex vivo-expanded and activated natural killer (NK) cells in combination with exogenous cytokines (for example, IL-2, IL-12, IL-21, IL-18, IL-15, IL-7) or NK cells engineered to secrete or express membrane-bound or tethered cytokines (for example, IL-2, IL-12, IL-21, IL-18, IL-15, IL-7) on their surface for the treatment of glioblastoma (GBM) and other cancers. Prior to delivery, the cells may have been exposed under suitable conditions to an effective amount of IL-2, IL-12, IL-21, IL-18, IL-15, and/or IL-7 in culture. In particular embodiments, the cells comprise one or more exogenously provided interleukins that are not IL-15, although in alternative embodiments the cells comprise exogenously provided IL-15.

In specific embodiments, the disclosure encompasses methods of treating glioblastoma using adoptive cell therapy comprising NK cells. In particular aspects, the NK cells are effective particularly against glioblastoma stem cells, and the disclosure provides methods and compositions for enhancing NK cells against glioblastoma cells of any kind, including glioblastoma cells. The disclosure encompasses methods of killing glioblastoma stem cells in an individual with glioblastoma comprising administering to the individual an effective amount of NK cells engineered to express one or more exogenously provided IL and/or that have been cultured in the presence of one of more IL. In some embodiments, the glioblastoma stem cells are killed by NK cells that express one or more engineered receptors, and the engineered receptors may or may not target one or more antigens that are expressed on glioblastoma stem cells. In certain cases, glioblastoma stem cells are killed by NK cells that have been engineered to express one or more engineered receptors, that have been engineered to express one or more exogenous cytokines, and/or that have been cultured in the presence of one or more IL.

Embodiments of the disclosure include compositions comprising immune effector cells of any kind including natural killer (NK) cells, said cells comprising one or more exogenously provided IL, optionally wherein the IL is not IL-15, and wherein the cell comprises one or more engineered receptors. In particular embodiments, the IL is selected from the group consisting of IL-12, IL-21, IL-2, IL-15, IL-18, IL-7, and a combination thereof. In specific cases, the IL is IL-12, IL-21, or both. In any embodiment of the disclosure, the IL may be secreted, tethered, or membrane bound in the cell. As used herein, "exogenously provided" may be further defined as being expressed from a vector in the cells and/or wherein the cells are externally exposed to the one or more IL.

In particular embodiments, engineered receptors utilized in cells of the disclosure are engineered antigen receptors, such as a chimeric antigen receptor (CAR) or a T cell receptor (TCR). The antigen may be a cancer antigen, including a solid tumor antigen, or it may be an antigen associated with a pathogen. In cases wherein the antigen is a cancer antigen, specific examples include an antigen selected from the group consisting of 5T4, 8H9, $\alpha_v\beta_6$ integrin, BCMA, B7-H3, B7-H6, CAIX, CA9, CD5, CD19, CD20, CD22, CD30, CD33, CD38, CD44, CD44v6, CD44v7/8, CD70, CD123, CD138, CD171, CEA, CSPG4, CS1, CLL1, CD99, DLL3, EGFR, EGFR family including ErbB2 (HER2), EGFRvIII, EGP2, EGP40, ERBB3, ERBB4, ErbB3/4, EPCAM, EphA2, EpCAM, FAP, FBP, fetal AchR, FRα, GD2, GD3, Glypican-3 (GPC3), HLA-A1+MAGE1, HLA-A1+NY-ESO-1, IL-11Rα, IL-13Rα2, Lambda, Lewis-Y, L1CAM, Kappa, KDR, MCSP, Mesothelin, Muc1, Muc16, NCAM, NKG2D Ligands, NY-ESO-1, PRAME, PSC1, PSCA, PSMA, ROR1, SP17, Survivin, TAG72, TEMs, HMW-MAA, VEGFR2, and a combination thereof. In some embodiments, the engineered receptor is a cytokine receptor, chemokine receptor, or homing receptor, or a cell may have a combination of these.

In particular embodiments, the cells of the disclosure are cells, including NK cells, that comprise a suicide gene. In some cases, the cell is reduced or inhibited in expression of one or more of endogenous genes selected from the group consisting of TDAG8, NKG2A, SIGLEC-7, LAGS, TIM3, CISH, FOXO1, TGFBR2, TIGIT, CD96, ADORA2, NR3C1, PD1, PDL-1, PDL-2, CD47, SIRPA, SHIP1, ADAM17, RPS6, 4EBP1, CD25, CD40, IL21R, ICAM1, CD95, CD80, CD86, IL10R, CD5, CD7, and a combination thereof.

Embodiments of the disclosure include populations of any cells encompassed herein.

In one embodiment, there are methods of treating cancer in an individual, comprising the step of administering a therapeutically effective amount of any of the compositions encompassed herein. In some cases, the cancer cells in the individual have increased expression of NK ligands, such as MICA/B, ULBP1, ULBP2/5, ULBP3, B7-H6, CD112, CD155, HLA-ABC, HLA-DR, HLA-3, or a combination thereof. The engineered NK cells may express one or more engineered antigen receptors that target one or more of these NK ligands, or that may target other targets. The compositions may be provided to the individual intracranially, by injection, intravenously, intraarterially, intraperitoneally, intratracheally, intratumorally, intramuscularly, endoscopically, intralesionally, intracranially, percutaneously, subcutaneously, regionally, by perfusion, in a tumor microenvironment, or a combination thereof.

For cancer treatments, the cancer may be a solid tumor or is not a solid tumor. The cancer may be of the lung, brain, breast, blood, skin, pancreas, liver, colon, head and neck, kidney, thyroid, stomach, spleen, gallbladder, bone, ovary, testes, endometrium, prostate, rectum, anus, cervix, or is hematological. In specific cases, the cancer is glioblastoma.

In treatment method embodiments of the disclosure, the individual may be a mammal, such as a human, dog, cat, horse, cow, sheep, pig, or rodent. The individual may be administered one or more additional cancer therapies, including surgery, radiation, chemotherapy, hormone therapy, immunotherapy, or a combination thereof. In some embodiments, any method of the disclosure further comprises the step of diagnosing cancer in the individual. In some embodiments, any method of the disclosure further comprises the step of generating the cells. Any cells utilized herein may be autologous or allogeneic with respect to the individual.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which:

(FIG. 1A) NK cells were co-cultured with Cr51 labeled GSC for 4 hours in different ratios (n=4) and Cr51 release measured. (FIG. 1B) Expression of NK ligands on GSCs and astrocytes.

DETAILED DESCRIPTION

I. Examples of Definitions

Figure 1B:
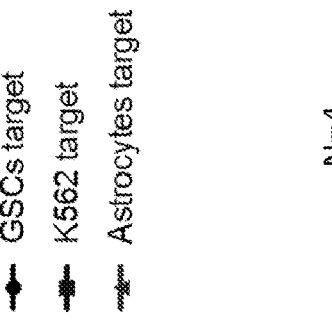
FIGS. 1A and 1B. Glioblastoma stem cells (GSCs) but not astrocytes are highly susceptible to NK-mediated lysis.

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

The term "engineered" as used herein refers to an entity that is generated by the hand of man, including a cell, nucleic acid, polypeptide, vector, and so forth. In at least some cases, an engineered entity is synthetic and comprises elements that are not naturally present or configured in the manner in which it is utilized in the disclosure.

The term "exogenous" as used herein refers to a polynucleotide (such as one encoding a gene product or part of a gene product) that is not present endogenously in a mammalian cell, such as an immune cell, or is synthetically generated outside of a mammalian cell, such as by recombinant technology. In a specific case, a particular gene product may be provided to a cell exogenously, and the cell may or may not also express the corresponding endogenous gene product in the cell.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also include reducing the intensity, effect, symptoms and/or burden of a disease or condition prior to onset or recurrence of the disease or condition.

The terms "subject" or "individual" as used herein are interchangeable and generally refer to an individual in need of treatment for a medical condition. In specific cases, the individual has or is suspected of having cancer. The subject can be any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals. The subject can be a patient, e.g., have or be suspected of having a disease (that may be referred to as a medical condition), such as benign or malignant neoplasias, or cancer. The subject may be undergoing or having undergone treatment. The subject may be asymptomatic. The subject may be healthy individuals but that are desirous of prevention of cancer. The "subject" or "individual", as used herein, may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants and includes in utero individuals. It is not intended that the term connote a need for medical treatment, therefore, an individual may voluntarily or involuntarily be part of experimentation whether clinical or in support of basic science studies. In alternative cases, the subject or individual is in need of pathogen treatment.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of one or more symptoms of the disease or condition, or the delaying of the onset or progression of the disease or condition. Treatment does not necessarily indicate complete eradication or cure of the disease or condition, or associated symptoms thereof. Treatment may include reducing the severity of one or more symptoms of a medical condition.

Embodiments of the present disclosure utilize immune effector cells, such as NK cells, for the immunotherapy of any kind of cancer, including glioblastoma. In particular embodiments, the immune effector cells are NK cells. NK cells are suitable as therapeutic effectors against highly heterogeneous tumors such as GBM, because unlike T and B lymphocytes, they do not possess rearranged V(D)J receptors and are not restricted by major histocompatibility complex (MHC)-bound antigen presentation. Instead, their effector function is dictated by the integration of signals received through germline-encoded receptors that can recognize multiple ligands on cancer targets without particular antigen specificity or requirement for co-stimulation.

Figure 1A:
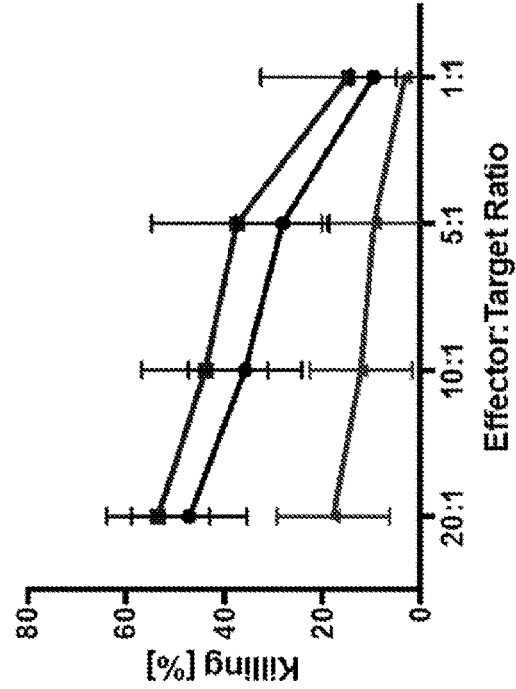

NK cells comprise one of the most abundant lymphoid subsets infiltrating glioblastoma (GBM), supporting the role for NK cells in the immune surveillance of this disease. Moreover, it is shown herein that GBM stem cells (GSCs), but not normal astrocytes, express many of the ligands recognized by NK activating receptors, such as MHC chain-related antigens (MICA/B) and the UL16-binding proteins (ULBPs)—recognized by NKG2D and CD155 (recognized by DNAM) and GSCs are highly susceptible to lysis by allogeneic healthy NK cells in vitro (FIG. 1A). Thus, a major advantage of NK cell immunotherapy over CAR T cells for GBM is their inherent ability to target multiple antigens on GSCs through their germ-line encoded receptors, without the need to target a specific antigen using a CAR. This property of NK cells may overcome the challenges related to antigen escape and tumor heterogeneity observed for CAR T cell therapy, including in GBM. The present disclosure allows for further improvement of the activity of NK cells against GBM by exposing them to either one or more exogenous cytokines such as IL-2, IL-12, IL-21, IL-7, or IL-18, and/or to engineer them to express one or more cytokine genes to help with their effector function, persistence and trafficking. The NK cells may be further modified to specifically target glioblastoma cells, including by utilizing engineered antigen receptors that target antigens on glioblastoma cells.

Specific embodiments of the disclosure encompass the use of allogeneic NK cells in combination with one or more exogenous cytokines and/or NK cells genetically engineered to secrete or express one or more cytokines on their surface. Such cells may be utilized for an off-the-shelf therapy that reduces cost and extends this therapy to many patients.

II. Cytokines

Embodiments of the disclosure include immune effector cells that have been exposed to one or more cytokines externally (including in culture, for example) and/or the cells have been transfected with a vector that expresses one or more cytokines. Although the cytokines may be of any kind, in specific embodiments the cytokines are IL-2, IL-12, IL-15, IL-21, IL-7, or IL-18. In particular embodiments, however, the cytokine is not IL-15.

In particular embodiments, the one or more exogenously provided cytokines that are expressed from a vector in the cells are membrane bound. Any of the cytokines may be membrane bound and expressed on the surface of NK cells, as the cytokine may be attached heterologously to the transmembrane domain of a membrane attachment molecule of any kind, e.g., B7-1, CD40, CD28, CD8, GMCSF receptor, IgG1, or IgG4.

In some cases, one or more cytokines are present on the same vector molecule as another gene product, such as an engineered receptor, although in other cases they are on separate molecules. In particular embodiments, one or more cytokines are co-expressed from the same vector as one or more engineered receptors. One or more cytokines may be produced as a separate polypeptide from an antigen-specific receptor. In specific cases, the cytokine induces development and cell proliferation of NK cells, promotes the eradication of established tumors via alleviating functional suppression of tumor-resident cells, and/or inhibits activation-induced cell death. Other cytokines are envisioned. These include, but are not limited to chemokines and other molecules that contribute to the activation and proliferation of cells used for human application.

In specific embodiments, NK cells express one or more exogenously provided cytokines. The cytokine may be exogenously provided to the cells because it is expressed from an expression vector within a feeder cell or could be added directly to the NK cell culture. In an alternative case, an endogenous cytokine in the cell is upregulated upon manipulation of regulation of expression of the endogenous cytokine, such as genetic recombination at the promoter site(s) of the cytokine. In cases wherein the cytokine is provided on an expression construct to the cell, the cytokine may be encoded from the same vector as one that expresses another gene product, such as a suicide gene. The cytokine may be expressed as a separate polypeptide molecule as a suicide gene and as a separate polypeptide from an engineered receptor of the cell. In some embodiments, the present disclosure concerns co-utilization of CAR and/or TCR vectors with a cytokine that is not IL-15.

III. Immune Effector Cells

The present disclosure encompasses immune effector cells of any kind that have one or more exogenously provided interleukins, wherein the interleukin is not IL-15, and optionally wherein the cells comprise one or more engineered receptors and/or other heterologous gene products. In specific embodiments, the exogenously provided IL to the cell is a direct or indirect result of deliberate manipulation of the cells by the hand of man. This is true whether the cells are exposed externally to one or more cytokines (for example, in culture) and/or whether the cells have been transfected to express one or more IL from a vector (that may or may not have integrated into the cell genome). The manipulation of the immune effector cells in such a manner may be by any mechanism. The immune effector cells may be NK cells, T cells, T regulatory cells, iNKT cells, B cells, MSCs, etc.

In cases wherein the immune effector cells have one or more exogenously provided interleukins, the cells may have been exposed externally to one or more cytokines by the process of being cultured in a media that comprises the one or more cytokines. A range of concentrations of cytokine in the media may be, e.g., 0.1 ng to 1000 ng; 0.1 ng to 750 ng; 0.1 ng to 500 ng; 0.1 to 250 ng; 0.1 to 100 ng; 0.1 to 75 ng; 0.1 to 50ng; 0.1 to 25ng; 0.1 to 10 ng; and so forth. A range of concentrations of cytokine in the media may be, e.g., 1 unit to 5000 units; 1 unit to 4000 units; 1 unit to 3000 units; 1 unit to 2000 units; 1 unit to 1000 units; 1 unit to 750 units; 1 unit to 500 units; 1 unit to 250 units; 1 unit to 100 units; 1 unit to 75 units; 1 unit to 50 units; 1 unit to 25 units; and so forth. In some cases, the cytokine(s) is in the media for the entirety of the time that the cells are cultured, whereas in other cases the cytokine(s) are added to the culture at a later point in time of the culture. The cytokine(s) may be present in the culture media at the first, second, third, fourth, or later passages, or a combination thereof.

The present disclosure encompasses immune effector cells of any kind, including conventional T cells, gamma-delta T cells, NK cells, NK T cells, invariant NK T cells, regulatory T cells, macrophages, B cells, dendritic cells, tumor-infiltrating lymphocytes, or a mixture thereof. The cells may be allogeneic, autologous, or xenogeneic with respect to an individual, including an individual in need of the cells, such as an individual with cancer.

In particular embodiments, the immune effector cells are modified by the hand of man to express or otherwise produce one or more cytokines, and these are not the endogenous cytokines in the cell, such as being recombinant. The immune effector cells may be modified in additional ways, such as by expressing an additional heterologous protein, such as an engineered receptor, a suicide gene, a combination thereof, and so forth. The cells may also be modified to have reduced or inhibited expression of one or more endogenous genes.

When the immune effector cells have been modified in more than one way, the order in which the immune effector cell is modified may be of any kind. For example, immune effector cells expressing an exogenously provided cytokine (and/or being exposed externally to one or more cytokines, such as in culture) may be transfected with one or more engineered receptors. In other cases, immune effector cells expressing one or more engineered receptors may be transfected with an exogenously provided cytokine and/or is exposed to one or more cytokines in culture.

In particular embodiments, the immune effector cells comprising one or more exogenously provided IL that is not IL-15 is the same cell that is modified to express an engineered receptor, such as an antigen receptor. Any immune effector cell encompassed by the present disclosure expresses an antigen receptor that may be of any kind, including a receptor directed towards an antigen that is a cancer antigen that may also be a solid tumor antigen. In specific embodiments, the receptor is a chimeric antigen receptor or a T-cell receptor, for example. The immune effector cells may be specifically designed to comprise one or more exogenously provided IL and may also be specifically designed to express an antigen receptor that targets an antigen on cancer cells in the individual. That is, the cells may be tailored to include one or more antigen receptors that target antigens known to be present on cancer cells of the individual.

In particular embodiments, cells of the present disclosure are produced for the purpose of being used as off-the-shelf cells. For example, cells that comprise one or more exogenously provided IL may be present in a repository, for example, and they may be obtained from the repository and engineered to have a further modification other than expressing an exogenously provided cytokine(s). In other cases, cells that have a modification other expressing an exogenously provided cytokine are obtained from a repository and are engineered to express one or more exogenously provided cytokines. Following such modifications to the cells after obtaining them from a repository, the cells may be stored, or an effective amount of the cells are provided to an individual in need thereof.

Any immune effector cells may be obtained from any form of repository, such as from being cryogenically preserved, and may be further modified. The cells may be stored as having an expression construct that expresses one or more cytokines and later be obtained and modified also to express a particular one or more engineered antigen receptors of interest, such as receptors that are engineered to target an antigen tailored to a particular cancer for an individual in need. The cells may be stored as having an expression construct that expresses one or more engineered antigen receptors of interest, such as receptors that target an antigen for a particular cancer, and thereafter they are modified to express one or more exogenous cytokines in need. Prior to or after storage, the cells may be modified to comprise a suicide gene, and in some cases the suicide gene is expressed from the same vector as the respective cytokine or engineered antigen receptor.

In particular embodiments, the immune effector cells comprise one or more exogenously provided IL and also express one or more engineered antigen-targeting receptors and/or express at least one suicide gene. In some cases for cells comprising one or more exogenously provided IL, different vectors encode the antigen-targeting receptor(s) vs. encode the suicide gene(s) and/or exogenous cytokine(s). In other cases, they (or a subset) are on the same vector. The immune effector cells, including NK cells, may be derived from any suitable source, such as from cord blood, peripheral blood, induced pluripotent stem cells (iPSCs), hematopoietic stem cells (HSCs), bone marrow, or a mixture thereof. The NK cells may be derived from a cell line such as, but not limited to, NK-92 cells, for example. The NK cell may be a cord blood mononuclear cell, such as a CD56+ NK cell.

In some cases, the immune effector cells (including NK cells) comprising one or more exogenously provided IL have been expanded in the presence of an effective amount of universal antigen presenting cells (UAPCs), including in any suitable ratio. The cells may be cultured with the UAPCs at a ratio of 10:1 to 1:10; 9:1 to 1:9; 8:1 to 1:8; 7:1 to 1:7; 6:1 to 1:6; 5:1 to 1:5; 4:1 to 1:4; 3:1 to 1:3; 2:1 to 1:2; or 1:1, including at a ratio of 1:2, for example. In some cases, the NK cells were expanded in the presence of IL-2, such as at a concentration of 10-500, 10-400, 10-300, 10-200, 10-100, 10-50, 100-500, 100-400, 100-300, 100-200, 200-500, 200-400, 200-300, 300-500, 300-400, or 400-500 U/mL.

Following genetic modification with any vector(s), the immune effector cells comprising one or more exogenously provided IL may be immediately delivered to an individual or may be stored (or some of the cells are delivered to an individual and the rest of the cells are stored). In certain aspects, following genetic modification, the cells may be propagated for days, weeks, or months ex vivo as a bulk population within about 1, 2, 3, 4, 5 days or more following gene transfer into cells. In a further aspect, the transfectants are cloned and a clone demonstrating presence of a single integrated or episomally maintained expression cassette or plasmid is expanded ex vivo. The clone selected for expansion demonstrates expression of one or more exogenously provided cytokines The recombinant immune cells may be expanded by stimulation with IL-2, or other cytokines that bind the common gamma-chain (e.g., IL-7, IL-12, IL-15, IL-21, and others). The recombinant immune cells may be expanded by stimulation with artificial antigen presenting cells. In a further aspect, any genetically modified cells may be cryopreserved.

Embodiments of the disclosure encompass immune effector cells comprise one or more exogenously provided IL and one or more engineered receptors, including one or more antigen receptors. The one or more engineered antigen receptors are generated by the hand of man, for example using recombinant techniques, and are not natural to the immune effector cell. Although the engineered receptor(s) may be of any kind, in specific embodiments the receptor is a chimeric antigen receptor, T-cell receptor, homing receptors, clustered regularly interspaced short palindromic repeats (CRISPR)/Cas9-mediated gene mutations, decoy receptors, cytokine receptors, chimeric cytokine receptors, combination thereof, and so forth.

Embodiments of the disclosure encompass cells comprising one or more exogenously provided IL and one or more suicide genes. The immune effector cell may comprise one or more exogenously provided IL and may comprise a recombinant nucleic acid that encodes a suicide gene of any kind. Examples of suicide genes include engineered nonsecretable (including membrane bound) tumor necrosis factor (TNF)-alpha mutant polypeptides (see PCT/US2019/062009, which is incorporated by reference herein in its entirety), and they may be affected by delivery of an antibody that binds the TNF-alpha mutant. Examples of suicide gene/prodrug combinations that may be used are Herpes Simplex Virus-thymidine kinase (HSV-tk) and ganciclovir, acyclovir, or FIAU; oxidoreductase and cyclohexinide; cytosine deaminase and 5-fluorocytosine; thymidine kinase thymidilate kinase (Tdk::Tmk) and AZT; and deoxycytidine kinase and cytosine arabinoside. The *E. coli* purine nucleoside phosphorylase, a so-called suicide gene that converts the prodrug 6-methylpurine deoxyriboside to toxic purine 6-methylpurine, may be utilized. Other suicide genes include CD20, CD52, inducible caspase 9, purine nucleoside phosphorylase (PNP), Cytochrome p450 enzymes (CYP), Carboxypeptidases (CP), Carboxylesterase (CE), Nitroreductase (NTR), Guanine Ribosyltransferase (XGRTP), Glycosidase enzymes, Methionine-$\alpha,\gamma$-lyase (MET), and Thymidine phosphorylase (TP), as examples.

The cells may be obtained from an individual directly or may be obtained from a depository or other storage facility. The cells as therapy may be autologous or allogeneic with respect to the individual to which the cells are provided as therapy.

The cells may be from an individual in need of therapy for a medical condition, and following their manipulation to comprise one or more exogenously provided IL, optional suicide gene, optional cytokine(s), and optional receptor(s) (using standard techniques for transduction and expansion for adoptive cell therapy, for example), they may be provided back to the individual from which they were originally sourced. In some cases, the cells are stored for later use for the individual or another individual.

The immune cells may be comprised in a population of cells, and that population may have a majority that comprise one or more exogenously provided IL and/or one or more suicide genes and/or one or more cytokines. A cell population may comprise 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of immune cells that comprise one or more exogenously provided IL and/or one or more suicide genes and/or one or more engineered receptor; each of these gene products may or may not be produced as separate polypeptides.

The immune cells may be produced to comprise one or more exogenously provided IL and/or one or more suicide genes and/or one or more cytokines for the intent of being modular with respect to a specific purpose. For example, cells may be generated, including for commercial distribution, comprising one or more exogenously provided IL and/or one or more suicide genes (or distributed with a nucleic acid that encodes a suicide gene for subsequent transduction), and a user may modify them to express one or more other genes of interest (including therapeutic genes) dependent upon their intended purpose(s). For instance, an individual interested in treating cancer cells may obtain or generate suicide gene-expressing cells (or heterologous cytokine-expressing cells) and modify them to comprise one or more exogenously provided IL, or vice versa.

In particular embodiments, NK cells are utilized, and the genome of the NK cells comprising one or more exogenously provided IL and/or one or more suicide genes and/or one or more engineered receptors may be modified. The genome may be modified in any manner, but in specific embodiments the genome is modified by CRISPR gene editing, for example. The genome of the cells may be modified to enhance effectiveness of the cells for any purpose. In specific cases, the cells are further modified by inhibition of expression of one or more genes. In some cases, the genes that are edited allow the cells to work more effectively in a tumor microenvironment. In specific cases, the genes are one or more of TDAG8, NKG2A, SIGLEC-7, LAGS, TIM3, CISH, FOXO1, TGFBR2, TIGIT, CD96, ADORA2, NR3C1, PD1, PDL-1, PDL-2, CD47, SIRPA, SHIP1, ADAM17, RPS6, 4EBP1, CD25, CD40, IL21R, ICAM1, CD95, CD80, CD86, IL10R, CD5, and CD7. In specific embodiments, one or more of these genes are knocked out or knocked down in the cells.

In cases wherein the cells are gene edited to have knocked out or knocked down expression of one or more genes, such gene editing may be carried out in any suitable manner. In some embodiments, any gene editing in the cells is carried out using one or more DNA-binding nucleic acids, such as alteration via an RNA-guided endonuclease (RGEN). For example, the alteration can be carried out using CRISPR and CRISPR-associated (Cas) proteins; in some embodiments, CpF1 is utilized instead of Cas9. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The CRISPR system can induce double stranded breaks (DSBs) at the target site, followed by disruptions or alterations as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2.

The CRISPR enzyme can be Cas9 (e.g., from *S. pyogenes* or *S. pneumonia*). In some cases, CpF1 may be used as an endonuclease instead of Cas9. The CRISPR enzyme can exert direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US 20110059502, incorporated herein by reference.

IV. Methods of Treatment

Embodiments of the disclosure include methods of treatment related to cancer immunotherapy, anti-pathogen immunotherapy, autoimmunity, or alloimmunity, for example. In specific case, the cancer immunotherapy and anti-pathogen immunotherapy comprise at least compositions comprising immune effector cells comprising one or more exogenously provided interleukins. The methods include providing to an individual with cancer and/or a pathogen an effective amount of immune effector cells comprising one or more exogenously provided interleukins.

In particular cases, an individual is provided an effective amount of cells comprising one or more exogenously provided interleukins. In specific cases, the cells are also expressing one or more engineered antigen receptors. In specific cases, the cells are also knocked-out using CRISPR/Cas9. The genetically engineered immune effector cells are used in various cellular therapies to increase their effectiveness against solid tumors, and these cellular therapies are provided to the individual.

As one example, NK cells comprising one or more exogenously provided interleukins express one or more CARs, and are genetically engineered to delete one or more endogenous genes for the purpose of increasing their effectiveness in the acidic TME of solid tumors, which in particular embodiments leads to expansion of this therapy to solid tumors. Moreover, this genetic engineering strategy is used in various other forms of cellular therapies, such as CAR-NK cells, T-cell receptor (TCR)-T cells, tumor-infiltrating lymphocytes (TILs), to potentiate them against various types of solid tumors.

In certain embodiments, cells of the disclosure are provided to an individual for the purpose of improving a medical condition, such as cancer of any kind and/or pathogen infection of any kind. Use of the cells contemplated herein, including pharmaceutical compositions comprising the same, are used for the prevention, treatment or amelioration of a cancerous disease, such as a tumorous disease, or a pathogen infection. In particular embodiments, the pharmaceutical composition of the present disclosure may be particularly useful in preventing, ameliorating and/or treating cancer, including cancers that may or may not be solid tumors, for example.

In particular embodiments, the present disclosure contemplates, in part, use of cells encompassed herein that can be administered either alone or in any combination with one or more other therapies, and in at least some aspects, together with a pharmaceutically acceptable carrier or excipient. In certain embodiments, any nucleic acid molecules or vectors may be stably integrated into the genome of the cells prior to deliver of the cells to the subject.

Any cells of the disclosure may be administered to the individual by injection, intravenously, intraarterially, intraperitoneally, intratracheally, intratumorally, intramuscularly, endoscopically, intralesionally, intracranially, percutaneously, subcutaneously, regionally, by perfusion, in a tumor microenvironment, or a combination thereof.

Furthermore, the disclosure relates to a method for the prevention, treatment or amelioration of a tumorous disease comprising the step of administering to a subject in the need thereof an effective amount of any cells that comprise one or more exogenously provided interleukins, as contemplated herein.

Possible indications for administration of the composition(s) of the cells are cancerous diseases, including tumorous diseases, including glioblastoma, B cell malignancies, multiple myeloma, lung, brain, breast, blood, skin, pancreas, liver, colon, head and neck, kidney, thyroid, stomach, spleen, gall bladder, bone, ovary, testes, endometrium, prostate, rectum, anus, or cervix, for example. Exemplary indications for administration of the composition(s) of the cells are cancerous diseases, including any malignancies that express one or more of certain antigens associated with the cancer of an individual. The administration of the composition(s) of the disclosure is useful for all stages and types of cancer, including for minimal residual disease, early cancer, advanced cancer, and/or metastatic cancer and/or refractory cancer, for example.

The disclosure further encompasses co-administration protocols with other compounds, e.g., bispecific antibody constructs, targeted toxins or other compounds, which act via immune cells. The clinical regimen for co-administration of the inventive compound(s) may encompass co-administration at the same time, before or after the administration of the other component. Particular combination therapies include chemotherapy, radiation, surgery, hormone therapy, or other types of immunotherapy.

Embodiments of the disclosure include methods of targeting a cellular immunotherapy to glioblastoma stem cells while excluding astrocytes from being targeted from the same cellular immunotherapy. The cellular immunotherapy may comprise immune effector cells of any kind including at least NK cells. The cellular immunotherapy may comprise immune effector cells comprising one or more exogenously provided cytokines.

Embodiments relate to a kit comprising constructs to produce the cells, a nucleic acid sequence as defined herein, a vector as defined herein and/or a host cell (such as an immune effector cell) as defined herein. It is also contemplated that the kit of this disclosure comprises a pharmaceutical composition as described herein above, either alone or in combination with further medicaments to be administered to an individual in need of medical treatment or intervention.

V. Genetically Engineered Receptors

The immune cells of the present disclosure comprising one or more exogenously provided interleukins may be modified further to express one or more non-endogenous gene products. The gene product may or may not be a genetically engineered receptor. The receptor may be of any kind, including a receptor for an antigen, chemokine, or cytokine, for example. In cases wherein the receptor is for an antigen, the antigen may be a cancer antigen, including a solid tumor antigen.

The immune effector cells comprising one or more exogenously provided interleukins may be genetically engineered to express antigen receptors that target specific antigens, and such cells may be specifically designed to target one or more antigens that are present on cancer cells of an individual.

In specific embodiments, the immune effector cells comprising one or more exogenously provided interleukins may comprise an engineered antigen receptor, such as engineered TCRs or CARs. For example, the immune cells may be NK cells that are modified to express one or more CARs and/or TCRs having antigenic specificity for one or more specific antigens. In some aspects, the immune cells are engineered to express an antigen-specific CAR or antigen-specific TCR by knock-in of the CAR or TCR for example using CRISPR.

Suitable methods of modification are known in the art. See, for instance, Sambrook and Ausubel, supra. For example, the cells may be transduced to express a TCR having antigenic specificity for a cancer antigen using transduction techniques described in Heemskerk et al., 2008 and Johnson et al., 2009.

In some embodiments, the cells comprise one or more nucleic acids introduced via genetic engineering that encode one or more antigen receptors and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., 2013; Davila et al., 2013; Turtle et al., 2012; Wu et al., 2012. In some aspects, the genetically engineered antigen receptors include a CAR as described in U.S. Pat. No. 7,446,190, and those described in International Patent Application Publication No.: WO/2014055668 A1.

When the engineered receptors are antigen receptors, the antigen may be selected from the group consisting of 5T4, 8H9, $\alpha_v\beta_6$ integrin, BCMA, B7-H3, B7-H6, CAIX, CA9, CD5, CD19, CD20, CD22, CD30, CD33, CD38, CD44, CD44v6, CD44v7/8, CD70, CD123, CD138, CD171, CEA, CSPG4, CS1, CLL1, CD99, DLL3, EGFR, EGFR family including ErbB2 (HER2), EGFRvIII, EGP2, EGP40, ERBB3, ERBB4, ErbB3/4, EPCAM, EphA2, EpCAM, FAP, FBP, fetal AchR, FRα, GD2, GD3, Glypican-3 (GPC3), HLA-A1+MAGE1, HLA-A1+NY-ESO-1, IL-11Rα, IL-13Rα2, Lambda, Lewis-Y, L1CAM, Kappa, KDR, MCSP, Mesothelin, Muc1, Muc16, NCAM, NKG2D Ligands, NY-ESO-1, PRAME, PSC1, PSCA, PSMA, ROR1, SP17, Survivin, TAG72, TEMs, HMW-MAA, and VEGFR2.

A. Chimeric Antigen Receptors

In some embodiments, the antigen-specific CAR comprises: a) one or more intracellular signaling domains, b) a transmembrane domain, and c) an extracellular domain comprising an antigen binding region that targets, including specifically binds, the desired antigen.

In some embodiments, the engineered antigen receptors include CARs, including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

Certain embodiments of the present disclosure concern the use of nucleic acids, including nucleic acids encoding an antigen-specific CAR polypeptide, including a CAR that has been humanized to reduce immunogenicity (hCAR), comprising at least one intracellular signaling domain, a transmembrane domain, and an extracellular domain comprising one or more signaling motifs. In certain embodiments, the antigen-specific CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human antigen CAR nucleic acids may be human genes used to enhance cellular immunotherapy for human patients. In a specific embodiment, the disclosure includes a full-length antigen-specific CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, DAP12, and 4-1BB (CD137). In addition to a primary signal initiated by CD3ζ, an additional signal provided by a human costimulatory receptor inserted in a human CAR is important for full activation of NK cells and could help improve in vivo persistence and the therapeutic success of the adoptive immunotherapy.

In some embodiments, antigen-specific CAR is constructed with specificity for the antigen, such as the antigen being expressed on a normal or non-diseased cell type or on a diseased cell type. Thus, the CAR typically includes in its extracellular portion one or more antigen-binding molecules, such as one or more antigen-binding fragment, domain, or portion, or one or more antibody variable domains, and/or antibody molecules. In some embodiments, the antigen-specific CAR includes an antigen-binding portion or portions of an antibody molecule, such as a single-chain antibody fragment (scFv) derived from the variable heavy (VH) and variable light (VL) chains of a monoclonal antibody (mAb).

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD 16, CD22, CD33, CD37, CD64, CD80, CD86, CD134, CD137, CD154, ICOS/CD278, GITR/CD357, NKG2D, and DAP molecules. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

In certain embodiments, the platform technologies disclosed herein to genetically modify immune cells, such as NK cells, comprise (i) non-viral gene transfer using an electroporation device (e.g., a nucleofector), (ii) CARs that signal through endodomains (e.g., CD28/CD3-ζ, CD137/CD3-ζ, or other combinations), (iii) CARs with variable lengths of extracellular domains connecting the CD70-recognition domain to the cell surface, and, in some cases, (iv) artificial antigen presenting cells (aAPC) derived from K562 to be able to robustly and numerically expand CAR⁺ immune cells (Singh et al., 2008; Singh et al., 2011).

B. T Cell Receptors (TCR)

In some embodiments, the genetically engineered antigen receptors include recombinant TCRs and/or TCRs cloned from naturally occurring T cells. A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a major histocompatibility complex (MHC) receptor. In some embodiments, the TCR is in the αβ form.

Typically, TCRs that exist in αβ and γδ forms are generally structurally similar, but T cells expressing them may have distinct anatomical locations or functions. A TCR can be found on the surface of a cell or in soluble form.

Generally, a TCR is found on the surface of T cells (or T lymphocytes) where it is generally responsible for recognizing antigens bound to MHC molecules. In some embodiments, a TCR also can contain a constant domain, a transmembrane domain and/or a short cytoplasmic tail (see, e.g., Janeway et al, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or "antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., 1990; Chothia et al., 1988; Lefranc et al., 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., a-chain, β-chain) can contain two immunoglobulin domains, a variable domain (e.g., $V_a$ or Vp; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., a-chain constant domain or $C_a$, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contain a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3 chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T cell hybridomas or other publicly available sources. In some embodiments, the T cells can be obtained from in vivo isolated cells. In some embodiments, a high-affinity T cell clone can be isolated from a patient, and the TCR isolated. In some embodiments, the T cells can be a cultured T cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al., 2009 and Cohen et al., 2005). In some embodiments, phage display is used to isolate TCRs against a target antigen (see, e.g., Varela-Rohena et al., 2008 and Li, 2005). In some embodiments, the TCR or antigen-binding portion thereof can be synthetically generated from knowledge of the sequence of the TCR.

VI. Vectors

In cases wherein the immune effector cell comprises a non-endogenous engineered gene product or exogenously provided gene product, such as one or more exogenously provided interleukins, the gene product may be delivered to the recipient immune effector cells by any suitable vector, including by a viral vector or by a non-viral vector. Examples of viral vectors include at least retroviral, lentiviral, adenoviral, or adeno-associated viral vectors. Examples of non-viral vectors include at least plasmids, transposons, lipids, nanoparticles, and so forth.

In cases wherein the immune cell is transduced with a vector encoding the antigen-targeting receptor and also requires transduction of another gene or genes into the cell, such as a suicide gene and/or cytokine and/or an optional therapeutic gene product, the antigen-targeting receptor, suicide gene, cytokine, and optional therapeutic gene may or may not be comprised on or with the same vector. In some cases, the antigen-targeting CAR, suicide gene, cytokine, and optional therapeutic gene are expressed from the same vector molecule, such as the same viral vector molecule. In such cases, the expression of the cytokine, optional antigen-targeting receptor, optional suicide gene, and optional therapeutic gene may or may not be regulated by the same regulatory element(s). When the cytokine, optional antigen-targeting CAR, optional suicide gene, and optional therapeutic gene are on the same vector, they may or may not be expressed as separate polypeptides. In cases wherein they are expressed as separate polypeptides, they may be separated on the vector by a 2A element or IRES element (or both kinds may be used on the same vector once or more than once), for example.

A. General Embodiments

One of skill in the art would be well-equipped to construct a vector through standard recombinant techniques (see, for example, Sambrook et al., 2001 and Ausubel et al., 1996, both incorporated herein by reference) for the expression of the antigen receptors of the present disclosure.

1. Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells may be comprised of multiple genetic elements. The cellular machinery is able to gather and integrate the regulatory information conveyed by each element, allowing different genes to evolve distinct, often complex patterns of transcriptional regulation. A promoter used in the context of the present disclosure includes constitutive, inducible, and tissue-specific promoters, for example. In cases wherein the vector is utilized for the generation of cancer therapy, a promoter may be effective under conditions of hypoxia.

2. Promoter/Enhancers

The expression constructs provided herein comprise a promoter to drive expression of the antigen receptor and other cistron gene products. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, for example, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp-) promoter systems. In addition to producing nucleic acid sequences of promoters and enhancers synthetically, sequences may be produced using recombinant cloning and/or nucleic acid amplification technology, including PCR™, in connection with the compositions disclosed herein. Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally, any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter, GADPH promoter, metallothionein promoter; and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at GenBank®, accession no. X05244, nucleotide 283-341) or a mouse mammary tumor promoter (available from the ATCC, Cat. No. ATCC 45007). In certain embodiments, the promoter is CMV IE, dectin-1, dectin-2, human CD11c, F4/80, SM22, RSV, SV40, Ad MLP, beta-actin, MHC class I or MHC class II promoter, however any other promoter that is useful to drive expression of the therapeutic gene is applicable to the practice of the present disclosure.

In certain aspects, methods of the disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

3. Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

As detailed elsewhere herein, certain 2A sequence elements could be used to create linked- or co-expression of genes in the constructs provided in the present disclosure. For example, cleavage sequences could be used to co-express genes by linking open reading frames to form a single cistron. An exemplary cleavage sequence is the equine rhinitis A virus (E2A) or the F2A (Foot-and-mouth disease virus 2A) or a "2A-like" sequence (e.g., *Thosea asigna* virus 2A; T2A) or porcine teschovirus-1 (P2A). In specific embodiments, in a single vector the multiple 2A sequences are non-identical, although in alternative embodiments the same vector utilizes two or more of the same 2A sequences. Examples of 2A sequences are provided in US 2011/0065779 which is incorporated by reference herein in its entirety.

4. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

5. Selection and Screenable Markers

In some embodiments, NK cells comprising a CD70-targeting receptor construct of the present disclosure may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

B. Multicistronic Vectors

In particular embodiments, the cytokine, optional antigen-targeting receptor, optional suicide gene, and/or optional therapeutic gene are expressed from a multicistronic vector (The term "cistron" as used herein refers to a nucleic acid sequence from which a gene product may be produced). In specific embodiments, the multicistronic vector encodes at least one cytokine, the suicide gene, and/or engineered receptor, such as a T-cell receptor and/or an additional non-antigen-targeting CAR. In some cases, the multicistronic vector encodes at least one antigen-targeting CAR, at least one suicide gene, and at least one cytokine. The cytokine may be of a particular type of cytokine, such as human or mouse or any species. In specific cases, the cytokine is IL-7, IL-12, IL-2, IL-18, and/or IL-21.

In certain embodiments, the present disclosure provides a flexible, modular system (the term "modular" as used herein refers to a cistron or component of a cistron that allows for interchangeability thereof, such as by removal and replacement of an entire cistron or of a component of a cistron, respectively, for example by using standard recombination techniques) utilizing a polycistronic vector having the ability to express multiple cistrons at substantially identical levels. The system may be used for cell engineering allowing for combinatorial expression (including overexpression) of multiple genes. In specific embodiments, one or more of the genes expressed by the vector include one, two, or more antigen receptors. The multiple genes may comprise, but are not limited to, CARs, TCRs, cytokines, chemokines, homing receptors, CRISPR/Cas9-mediated gene mutations, decoy receptors, cytokine receptors, chimeric cytokine receptors, and so forth. The vector may further comprise: (1) one or more reporters, for example fluorescent or enzymatic reporters, such as for cellular assays and animal imaging; (2) one or more cytokines or other signaling molecules; and/or (3) a suicide gene.

In specific cases, the vector may comprise at least 4 cistrons separated by cleavage sites of any kind, such as 2A cleavage sites. The vector may or may not be Moloney Murine Leukemia Virus (MoMLV or MMLV)-based including the 3' and 5' LTR with the psi packaging sequence in a pUC19 backbone. The vector may comprise 4 or more cistrons with three or more 2A cleavage sites and multiple ORFs for gene swapping. The system allows for combinatorial overexpression of multiple genes (7 or more) that are flanked by restriction site(s) for rapid integration through subcloning, and the system also includes at least three 2A self-cleavage sites, in some embodiments. Thus, the system allows for expression of multiple CARs, TCRs, signaling molecules, cytokines, cytokine receptors, and/or homing receptors. This system may also be applied to other viral and non-viral vectors, including but not limited to lentivirus, adenovirus AAV, as well as non-viral plasmids.

The modular nature of the system also enables efficient subcloning of a gene into each of the 4 cistrons in the polycistronic expression vector and the swapping of genes, such as for rapid testing. Restriction sites strategically located in the polycistronic expression vector allow for swapping of genes with efficiency.

Embodiments of the disclosure encompass systems that utilize a polycistronic vector wherein at least part of the vector is modular, for example by allowing removal and replacement of one or more cistrons (or component(s) of one or more cistrons), such as by utilizing one or more restriction enzyme sites whose identity and location are specifically selected to facilitate the modular use of the vector. The vector also has embodiments wherein multiple of the cistrons are translated into a single polypeptide and processed into separate polypeptides, thereby imparting an advantage for the vector to express separate gene products in substantially equimolar concentrations.

The vector of the disclosure is configured for modularity to be able to change one or more cistrons of the vector and/or to change one or more components of one or more particular cistrons. The vector may be designed to utilize unique restriction enzyme sites flanking the ends of one or more cistrons and/or flanking the ends of one or more components of a particular cistron.

Embodiments of the disclosure include polycistronic vectors comprising at least two, at least three, or at least four cistrons each flanked by one or more restriction enzyme sites, wherein at least one cistron encodes for at least one antigen receptor. In some cases, two, three, four, or more of the cistrons are translated into a single polypeptide and cleaved into separate polypeptides, whereas in other cases multiple of the cistrons are translated into a single polypeptide and cleaved into separate polypeptides. Adjacent cistrons on the vector may be separated by a self cleavage site, such as a 2A self cleavage site. In some cases each of the cistrons expresses separate polypeptides from the vector. On particular cases, adjacent cistrons on the vector are separated by an IRES element.

In certain embodiments, the present disclosure provides a system for cell engineering allowing for combinatorial expression, including overexpression, of multiple cistrons that may include one, two, or more antigen receptors, for example. In particular embodiments, the use of a polycistronic vector as described herein allows for the vector to produce equimolar levels of multiple gene products from the same mRNA. The multiple genes may comprise, but are not limited to, cytokines, CARs, TCRs, chemokines, homing receptors, CRISPR/Cas9-mediated gene mutations, decoy receptors, cytokine receptors, chimeric cytokine receptors, and so forth. The vector may further comprise one or more fluorescent or enzymatic reporters, such as for cellular assays and animal imaging. The vector may also comprise a suicide gene product for termination of cells harboring the vector when they are no longer needed or become deleterious to a host to which they have been provided.

In particular embodiments of the disclosure, at least one of the cistrons on the vector comprises two or more modular components, wherein each of the modular components within a cistron is flanked by one or more restriction enzyme sites. A cistron may comprise three, four, or five modular components, for example. In at least some cases, a cistron encodes an antigen receptor having different parts of the receptor encoded by corresponding modular components. A first modular component of a cistron may encode an antigen binding domain of the receptor. In addition, a second modular component of a cistron may encode a hinge region of the receptor. In addition, a third modular component of a cistron may encode a transmembrane domain of the receptor. In addition, a fourth modular component of a cistron may encode a first costimulatory domain. In addition, a fifth modular component of a cistron may encode a second costimulatory domain. In addition, a sixth modular component of a cistron may encode a signaling domain.

In particular aspects of the disclosure, two different cistrons on the vector each encode non-identical antigen receptors. Both antigen receptors may be encoded by a cistron comprising two or more modular components, including separate cistrons comprising two or more modular components. The antigen receptor may be a chimeric antigen receptor (CAR) and/or T cell receptor (TCR), for example.

In specific embodiments, the vector is a viral vector (retroviral vector, lentiviral vector, adenoviral vector, or adeno-associated viral vector, for example) or a non-viral vector. The vector may comprise a Moloney Murine Leukemia Virus (MMLV) 5' LTR, 3' LTR, and/or psi packaging element. In specific cases, the psi packaging is incorporated between the 5' LTR and the antigen receptor coding sequence. The vector may or may not comprise pUC19 sequence. In some aspects of the vector, at least one cistron encodes for a cytokine (interleukin 15 (IL-15), IL-7, IL-21, or IL-2, for example), chemokine, cytokine receptor, and/or homing receptor.

When 2A cleavage sites are utilized in the vector, the 2A cleavage site may comprise a P2A, T2A, E2A and/or F2A site.

In addition to one cistron encoding a CD70-targeting CAR, any cistron of the vector may comprise a suicide gene. Any cistron of the vector may encode a reporter gene. In specific embodiments, a first cistron encodes a suicide gene, a second cistron encodes a CD70-targeting CAR, a third cistron encodes a reporter gene, and a fourth cistron encodes a cytokine. In certain embodiments, a first cistron encodes a suicide gene, a second cistron encodes a CD70-targeting CAR, a third cistron encodes a second CAR or another antigen receptor, and a fourth cistron encodes a cytokine. In specific embodiments, different parts of the a CD70-targeting CAR and/or another receptor are encoded by corresponding modular components and a first component of the second cistron encodes an antigen binding domain, a second component encodes a hinge and/or transmembrane domain, a third component encodes a costimulatory domain, and a fourth component encodes a signaling domain.

In specific embodiments, at least one of the cistrons encodes a suicide gene. In some embodiments, at least one of the cistrons encodes a cytokine. In certain embodiments, at least one cistron encodes an antigen-targeting CAR. A cistron may or may not encode a reporter gene. In certain embodiments, at least two cistrons encode two different antigen receptors (e.g., CARs and/or TCRs). A cistron may or may not encode a reporter gene.

In particular configurations of the genetic cargo of interest, a single vector may comprise a cistron that encodes an antigen-targeting CAR and a cistron that encodes a second antigen receptor that is non-identical to the antigen-targeting receptor. In specific embodiments, the first antigen receptor encodes an antigen-targeting CAR and the second antigen receptor encodes a TCR, or vice versa. In particular embodiments, a vector comprising separate cistrons that respectively encode an antigen-targeting CAR and a second antigen receptor also comprises a third cistron that encodes a cytokine or chemokine and a fourth cistron that encodes a suicide gene. However, the suicide gene and/or the cytokine (or chemokine) may not be present on the vector.

In particular embodiments, at least one cistron comprises multiple component(s) themselves that are modular. For example, one cistron may encode a multi-component gene product, such as an antigen receptor having multiple parts; in specific cases the antigen receptor is encoded from a single cistron, thereby ultimately producing a single polypeptide. The cistron encoding multiple components may have the multiple components separated by 1, 2, 3, 4, 5, or more restriction enzyme digestion sites, including 1, 2, 3, 4, 5, or more restriction enzyme digestion sites that are unique to the vector comprising the cistron. In specific embodiments, a cistron having multiple components encodes an antigen receptor having multiple corresponding parts each attributing a unique function to the receptor. In a specific embodiment, each or the majority of components of the multi-component cistrons is separated by one or more restriction enzyme digestion sites that are unique to the vector, allowing the interchangeability of separate components when desired.

In specific embodiments, each component of a multi-component cistron corresponds to a different part of an encoded antigen receptor, such as an antigen-targeting CAR. In illustrative embodiments, component 1 may encode an antigen-binding domain of the receptor; component 2 may encode a hinge domain of the receptor; component 3 may encode a transmembrane domain of the receptor; component 4 may encode a costimulatory domain of the receptor, and component 5 may encode a signaling domain of the receptor. In specific embodiments, an antigen-targeting CAR may comprise one or more costimulatory domains, each separated by unique restriction enzyme digestion sites for interchangeability of the costimulatory domain(s) within the receptor.

In specific embodiments, there is a polycistronic vector having four separate cistrons where adjacent cistrons are separated by a 2A cleavage site, although in specific embodiments instead of a 2A cleavage site there is an element that directly or indirectly causes separate polypeptides to be produced from the cistrons (such as an IRES sequence). For example, four separate cistrons may be separated by three 2A peptide cleavage sites, and each cistron has restriction sites ($X_1$, $X_2$, etc.) flanking each end of the cistron to allow for interchangeability of the particular cistron, such as with another cistron or other type of sequence, and upon using standard recombination techniques. In specific embodiments, the restriction enzyme site(s) that flank each of the cistrons is unique to the vector to allow ease of recombination, although in alternative embodiments the restriction enzyme site is not unique to the vector.

In particular embodiments, the vector provides for a unique, second level of modularity by allowing for interchangeability within a particular cistron, including within multiple components of a particular cistron. The multiple components of a particular cistron may be separated by one or more restriction enzyme sites, including those unique to the vector, to allow for interchangeability of one or more components within the cistron. As an example, cistron 2 may comprise five separate components, although there may be 2, 3, 4, 5, 6, or more components per cistron. As an example, a vector may include cistron 2 that has five components each separated by unique enzyme restriction sites $X_9$, $X_{10}$, $X_{11}$, $X_{12}$, $X_{13}$, and $X_{14}$, to allow for standard recombination to exchange different components 1, 2, 3, 4, and/or 5. In some cases, there may be multiple restriction enzyme sites between the different components (that are unique, although alternatively one or more are not unique) and there may be sequence in between the multiple restriction enzyme sites (although alternatively there may not be). In certain embodiments, all components encoded by a cistron are designed for the purpose of being interchangeable. In particular cases, one or more components of a cistron are designed to be interchangeable, whereas one or more other components of the cistron may not be designed to be interchangeable.

In specific embodiments, a cistron encodes an antigen-targeting CAR molecule having multiple components. For example, cistron 2 may be comprised of sequence that encodes an antigen-targeting CAR molecule having its separate components represented by component 1, component 2, component 3, etc. The CAR molecule may comprise 2, 3, 4, 5, 6, 7, 8, or more interchangeable components. In a specific example, component 1 encodes a scFv; component 2 encodes a hinge; component 3 encodes a transmembrane domain; component 4 encodes a costimulatory domain (although there may also be component 4' that encodes a second or more costimulatory domain flanked by restriction sites for exchange); and component 5 encodes a signaling domain. In a particular example, component 1 encodes an scFv; component 2 encodes an IgG1 hinge and/or transmembrane domain; component 3 encodes CD28; and component 4 encodes CD3 zeta.

One of skill in the art recognizes in the design of the vector that the various cistrons and components must be configured such that they are kept in frame when necessary.

In a particular example, cistron 1 encodes a suicide gene; cistron 2 encodes an antigen-targeting CAR; cistron 3 encodes a reporter gene; cistron 4 encodes a cytokine; component 1 of cistron 2 encodes an scFv; component 2 of cistron 2 encodes IgG1 hinge; component 3 of cistron 2 encodes CD28; and component 4 encodes CD3 zeta.

A restriction enzyme site may be of any kind and may include any number of bases in its recognition site, such as between 4 and 8 bases; the number of bases in the recognition site may be at least 4, 5, 6, 7, 8, or more. The site when cut may produce a blunt cut or sticky ends. The restriction enzyme may be of Type I, Type II, Type III, or Type IV, for example. Restriction enzyme sites may be obtained from available databases, such as Integrated relational Enzyme database (IntEnz) or BRENDA (The Comprehensive Enzyme Information System).

Exemplary vectors may be circular and by convention, where position 1 (12 o'clock position at the top of the circle, with the rest of the sequence in clock-wise direction) is set at the start of 5' LTR.

In embodiments wherein self-cleaving 2A peptides are utilized, the 2A peptides may be 18-22 amino-acid (aa)-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (thosea asigna virus 2A) were also identified. The mechanism of 2A-mediated "self-cleavage" was discovered to be ribosome skipping the formation of a glycyl-prolyl peptide bond at the C-terminus of the 2A.

In specific cases, the vector may be a γ-retroviral transfer vector. The retroviral transfer vector may comprise a backbone based on a plasmid, such as the pUC19 plasmid (large fragment (2.63 kb) in between HindIII and EcoRI restriction enzyme sites). The backbone may carry viral components from Moloney Murine Leukemia Virus (MoMLV) including 5' LTR, psi packaging sequence, and 3' LTR. LTRs are long terminal repeats found on either side of a retroviral provirus, and in the case of a transfer vector, bracket the genetic cargo of interest, such as antigen-targeting CARs and associated components. The psi packaging sequence, which is a target site for packaging by nucleocapsid, is also incorporated in cis, sandwiched between the 5' LTR and the CAR coding sequence. Thus, the basic structure of an example of a transfer vector can be configured as such: pUC19 sequence-5' LTR-psi packaging sequence-genetic cargo of interest-3' LTR-pUC19 sequence. This system may also be applied to other viral and non-viral vectors, including but not limited to lentivirus, adenovirus AAV, as well as non-viral plasmids.

VII. Pharmaceutical Compositions

Provided herein are pharmaceutical compositions and formulations comprising immune effector cells as encompassed herein and a pharmaceutically acceptable carrier. The cells may be comprised in a media suitable for transfer to an individual and/or media suitable for preservation, such as cryopreservation, including prior to transfer to an individual.

Pharmaceutical compositions and formulations as described herein can be prepared by mixing the active ingredients (such as the cells) having the desired degree of purity with one or more optional pharmaceutically acceptable carriers (Remington's Pharmaceutical Sciences $22^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

VIII. Combination Therapies

In certain embodiments, the compositions and methods of the present embodiments involve an immune cell population (including NK cell population) in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, hormone therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

An immune cell therapy may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an immune cell therapy is "A" and an anti-cancer therapy is "B":

| A/B/A B/A/B B/B/A A/A/B A/B/B B/A/A A/B/B/B B/A/B/B |
| B/B/B/A B/B/A/B A/A/B/B A/B/A/B A/B/B/A B/B/A/A |
| B/A/B/A B/A/A/B A/A/A/B B/A/A/A A/B/A/A A/A/B/A |

Administration of any compound or cell therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclophosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegall); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel; gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin; procarbazine; plicomycin; gemcitabine, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells.

Antibody-drug conjugates have emerged as a breakthrough approach to the development of cancer therapeutics. Cancer is one of the leading causes of deaths in the world. Antibody—drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p9'7), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., Mycobacterium bovis, Plasmodium falciparum, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immuno-globulin (KIR), lymphocyte activation gene-3 (LAG3), pro-grammed death 1 (PD-1), T-cell immunoglobulin domain and mucin domain 3 (TIM-3) and V-domain Ig suppressor of T cell activation (VISTA). In particular, the immune check-point inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO 2015/016718; Pardoll, *Nat Rev Cancer,* 12(4): 252-64, 2012; both incor-porated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alter-native and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodi-ment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen bind-ing fragment thereof, an immunoadhesin, a fusion protein, or oligopeptide. Exemplary antibodies are described in U.S. Pat. Nos. 8,735,553, 8,354,509, and 8,008,449, all incorpo-rated herein by reference. Other PD-1 axis antagonists for use in the methods provided herein are known in the art such as described in U.S. Patent Application No. US 2014/0294898, US 2014/022021, and US 2011/0008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodi-ments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO 2009/114335. CT-011, also known as hBAT or hBAT-1, is an anti-PD-1 antibody described in WO 2009/101611. AMP-224, also known as B7-DCIg, is a PDL2-Fc fusion soluble receptor described in WO 2010/027827 and WO 2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Gen-Bank® accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respec-tively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a human-ized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as treme-limumab; formerly ticilimumab), U.S. Pat. No. 6,207,156; Hurwitz et al. (1998) *Proc Natl Acad Sci USA* 95(17): 10067-10071; Camacho et al. (2004) *J Clin Oncology* 22(145): Abstract No. 2505 (antibody CP-675206); and Mokyr et al. (1998) *Cancer Res* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Publication Nos. WO 2001/014424, WO 2000/037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody com-prises the heavy and light chain CDRs or VRs of ipilim-umab. Accordingly, in one embodiment, the antibody com-prises the CDR1, CDR2, and CDR3 domains of the VH region of ipilimumab, and the CDR1, CDR2 and CDR3 domains of the VL region of ipilimumab. In another embodi-ment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilim-umab).

Other molecules for modulating CTLA-4 include CTLA-4 ligands and receptors such as described in U.S. Pat. Nos. 5,844,905, 5,885,796 and International Patent Appli-cation Nos. WO 1995/001994 and WO 1998/042752; all incorporated herein by reference, and immunoadhesins such as described in U.S. Pat. No. 8,329,867, incorporated herein by reference.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IX. Kits of the Disclosure

Any of the compositions described herein may be comprised in a kit. In a non-limiting example, cells that comprise one or more exogenously provided interleukins, reagents to produce the cells, vectors, and reagents to produce vectors and/or components thereof may be comprised in a kit. In certain embodiments, NK cells may be comprised in a kit, and they may or may not yet be modified in any manner. Such a kit may or may not have one or more reagents for manipulation of cells. Such reagents include cytokines, small molecules, proteins, nucleic acids, antibodies, buffers, primers, nucleotides, salts, and/or a combination thereof, for example. Vectors may be provided that express one or more cytokines and/or one or more engineered antigen receptors, or reagents to manufacture either, may be included in the kit. Nucleotides that encode one or more cytokines, nucleotides that encode CRISPR reagents to KO one or more particular genes, suicide gene products, receptors, and so forth may be included in the kit. Proteins, such as cytokines or antibodies, including monoclonal antibodies, may be included in the kit.

Nucleotides that encode components of engineered CAR receptors or TCR receptors may be included in the kit, including reagents to generate same.

In particular aspects, the kit comprises the NK cell therapy of the disclosure and also another cancer therapy. In some cases, the kit, in addition to the cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

The kits may comprise suitably aliquoted compositions of the present disclosure. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also may generally contain a second, third or other additional container into which the additional components may be separately placed. However, various combinations of components may be comprised in a vial. The kits of the present invention also will typically include a means for containing the composition and any other reagent containers in close confinement for commercial sale. Such containers may include injection or blow-molded plastic containers into which the desired vials are retained.

EXAMPLES

The following examples are included to demonstrate certain non-limiting aspects of the disclosure. It should be appreciated by those of skill in the art that the techniques disclosed in the examples that follow represent techniques discovered by the inventors to function well in the practice of the disclosed subject matter. However, those of skill in the art should, in light of the present disclosure, appreciate that many changes can be made in the specific embodiments that are disclosed and still obtain a like or similar result without departing from the spirit and scope of the disclosed subject matter.

Example 1

NK Cell Immunotherapy for the Treatment of Glioblastoma

NK cells were tested for their ability to treat glioblastoma. NK cells can kill patient-derived glioblastoma stem cell lines (GCSs) but not normal astrocytes (FIG. 1). FIG. 1B shows differences in expression of select NK ligands between GCSs and Astrocytes.

Figure 2:
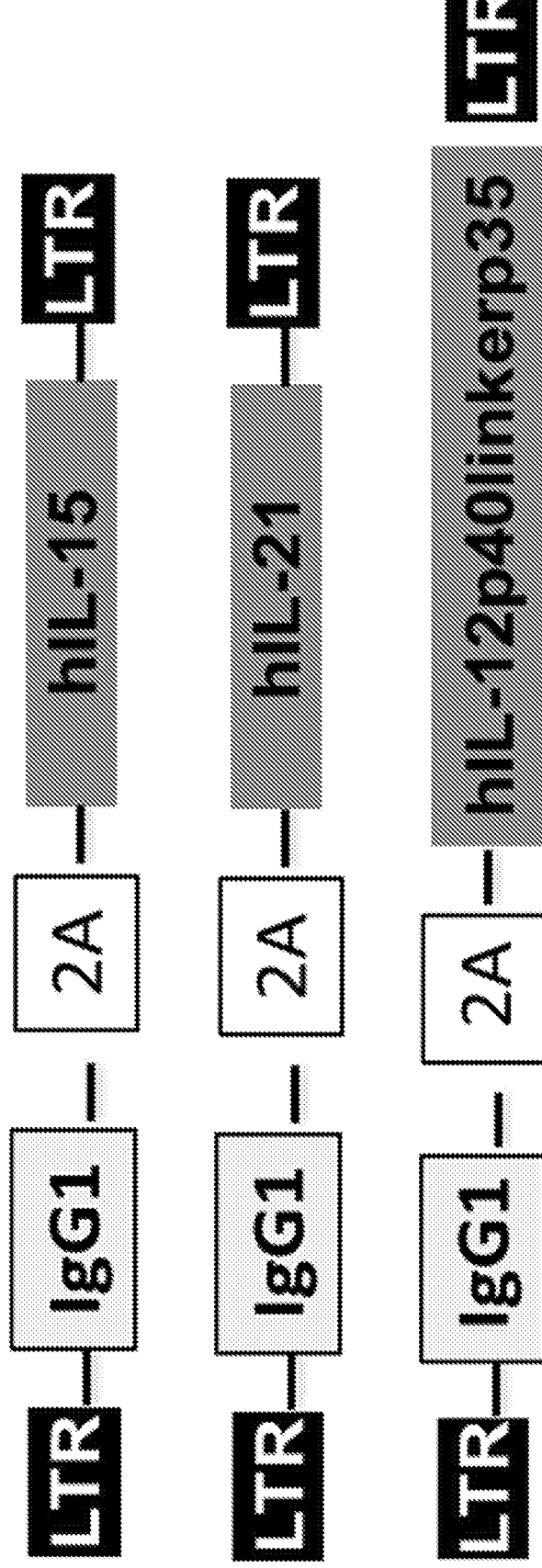
FIG. 2. Schematic representation of examples of retroviral vectors incorporating cytokine genes. hIL-12p40linkerp35 is human IL-12 in which the p35 and p40 subunits are artificially linked together with a linker.

NK cells can be engineered to express particular desired genes, such as one or more cytokine genes (for example, IL-15, IL-12, IL-21). Examples of specific constructs are presented in FIG. 2, where a 2A element separates production of a cytokine from production of IgG1, although they are on the same expression construct. In these specific examples, human IL-15, human IL-21, or human IL-12 are configured where the p35 and p40 subunits are artificially linked together with a linker. Such expression constructs may be present in any type of vector within the NK cells.

Figure 3A:
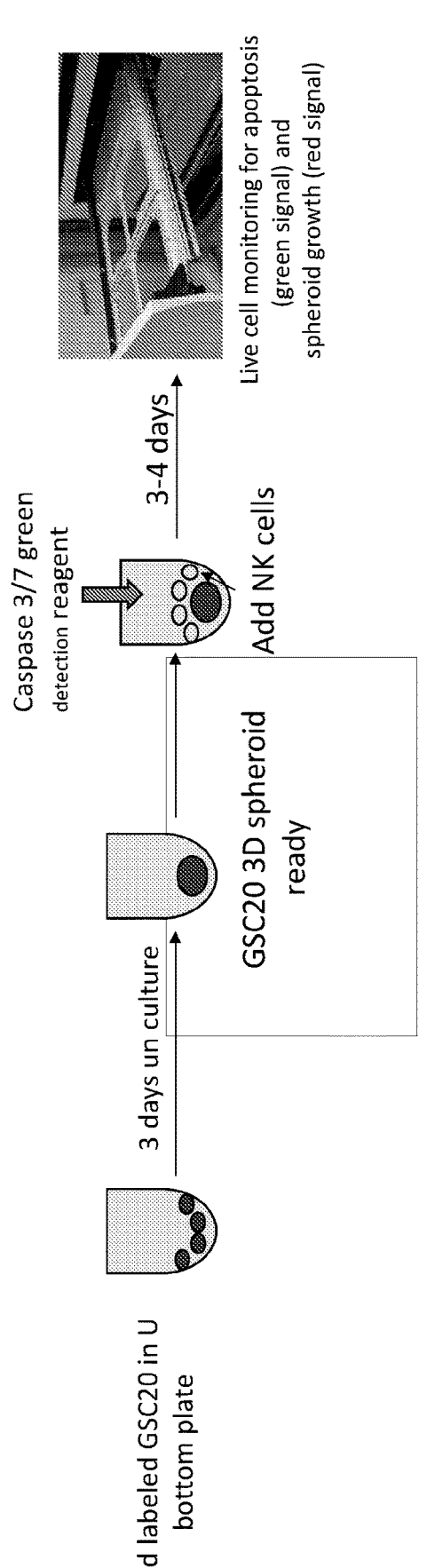
FIGS. 3A and 3B. Spheroid culture of patient-derived glioblastoma stem cell lines (GSC) as a 3-D tumor culture model (FIG. 3A) and cytotoxicity of cytokine-transduced CB-NK cells against GSCs targets (FIG. 3B). IL-12, IL-21 or IL-21 transduced NK cells (red (top line), green (third from top) and blue (second from top) lines) exert superior cytotoxicity against GSCs compared with non-transduced CB-NK (black line (bottom)) as shown by Incucyte® live imaging. Apoptotic cells are measured by caspase 3/7 green signal.
Figure 3B:
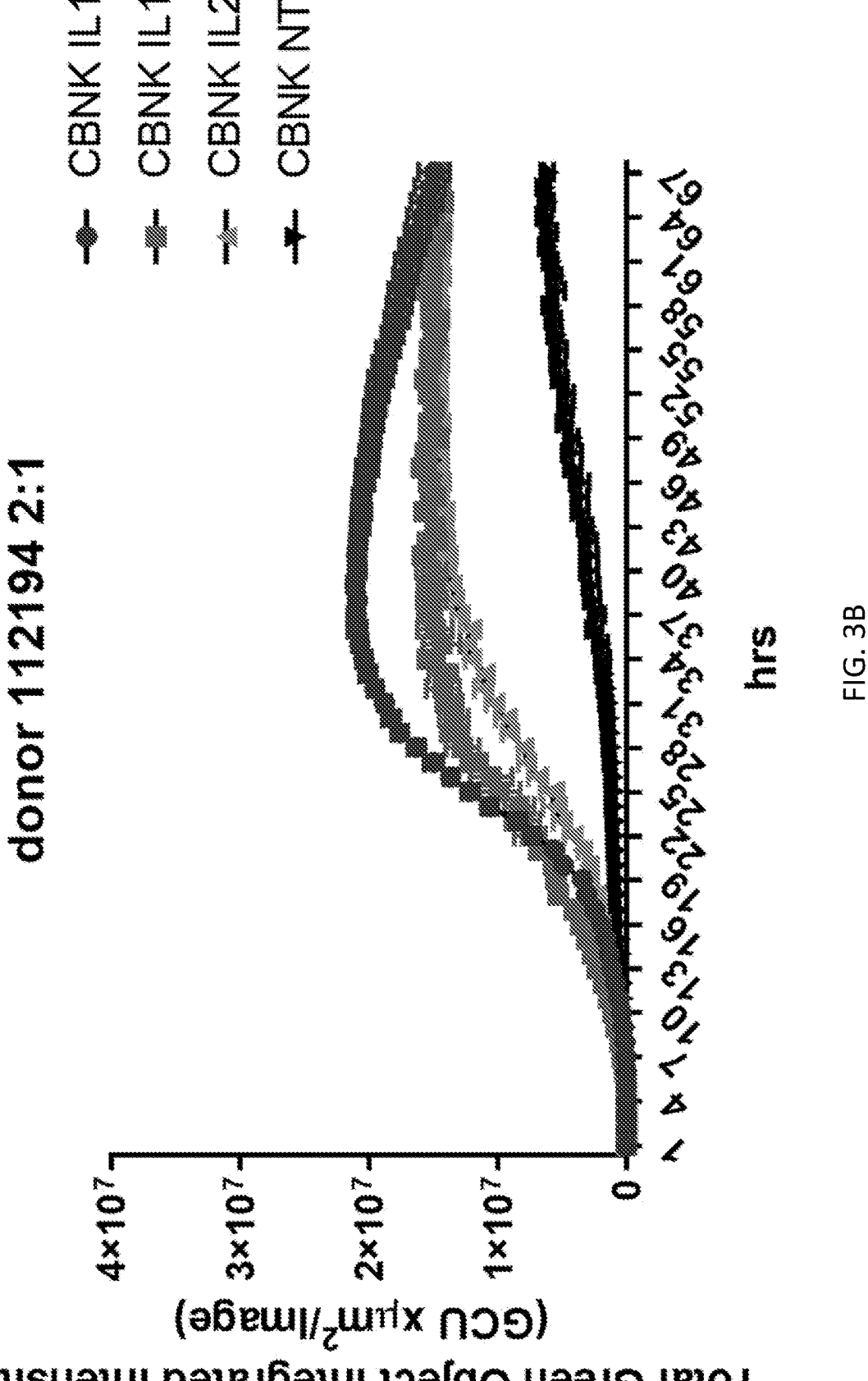

A 3-D tumor spheroid culture model of GSCs was employed to test the activity of cytokine-engineered NK cells (FIG. 3A). The tumor spheroid model simulates solid tumor masses. Killing assays were performed in Incucyte® device with live cell imaging of tumor cell growth and killing by NK cells. The noted cord blood derived cytokine-engineered NK cells (red, blue and green lines) exerted superior killing against patient-derived glioblastoma stem cell lines compared to non-transduced NK cells (black line) (FIG. 3B).

Figure 4A:
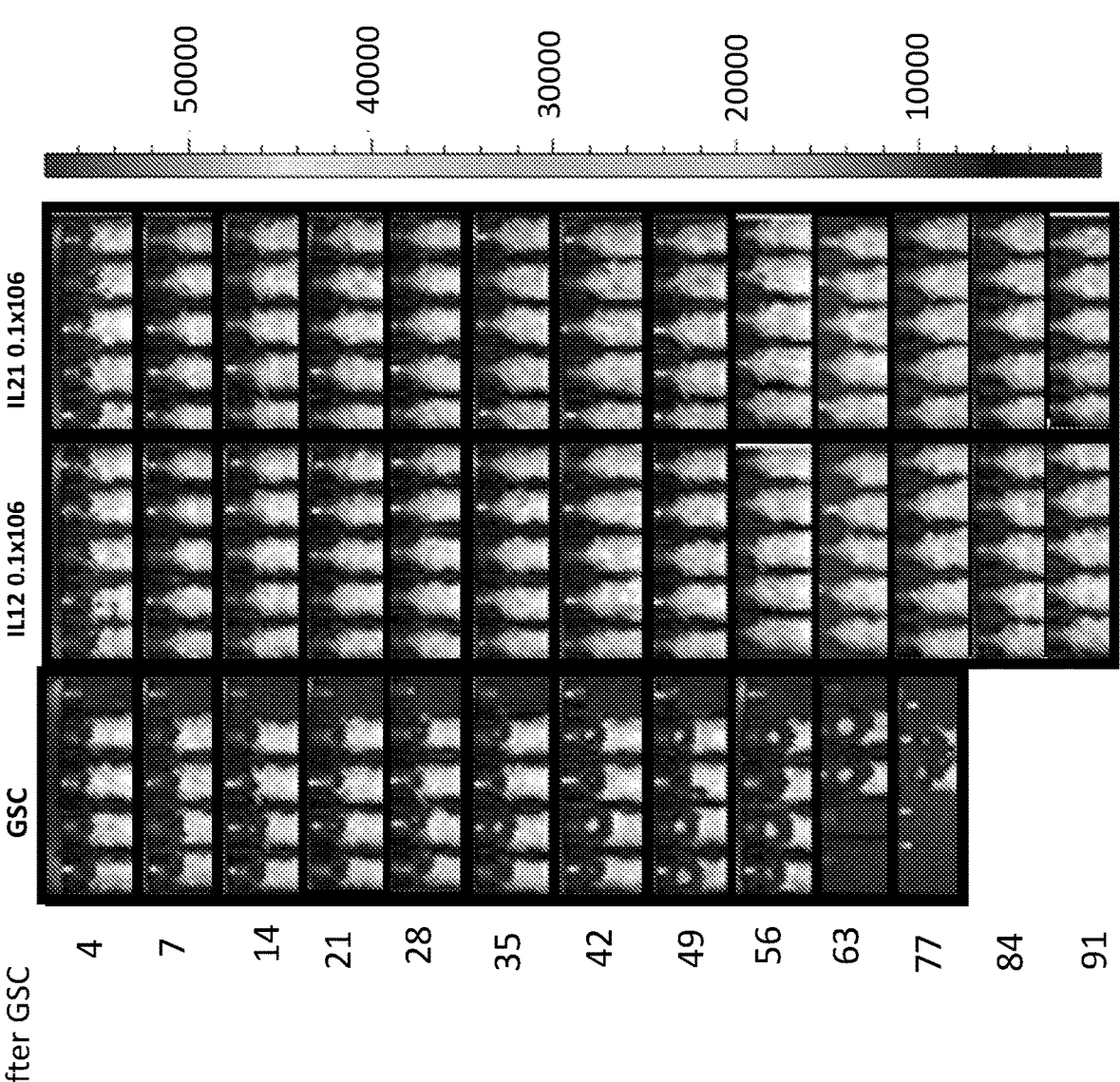
FIGS. 4A-4C. Comparison of non-transduced (NT) vs. IL12- and IL21-transduced NK cells in a patient-derived xenograft (PDX) model of FFluc-transduced GSCs. One infusion of IL-12 or IL21 transduced NK cells at a dose of $1 \times 10^5$ cells eradicates the tumor as shown by bioluminescence imaging (FIGS. 4A-4B) and results in long-term cure of the animals (FIG. 4C).
Figure 4B:
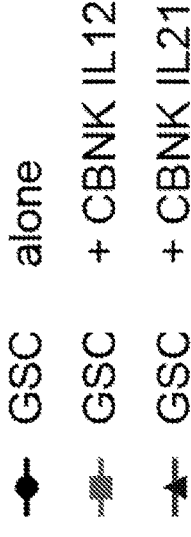
Figure 4B:
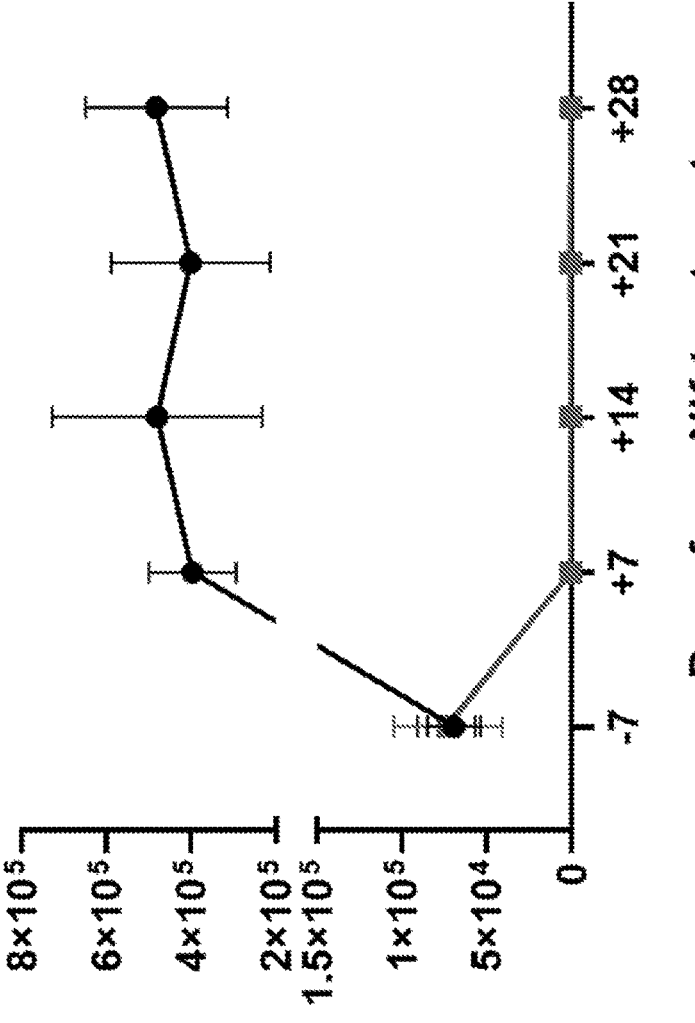
Figure 4C:
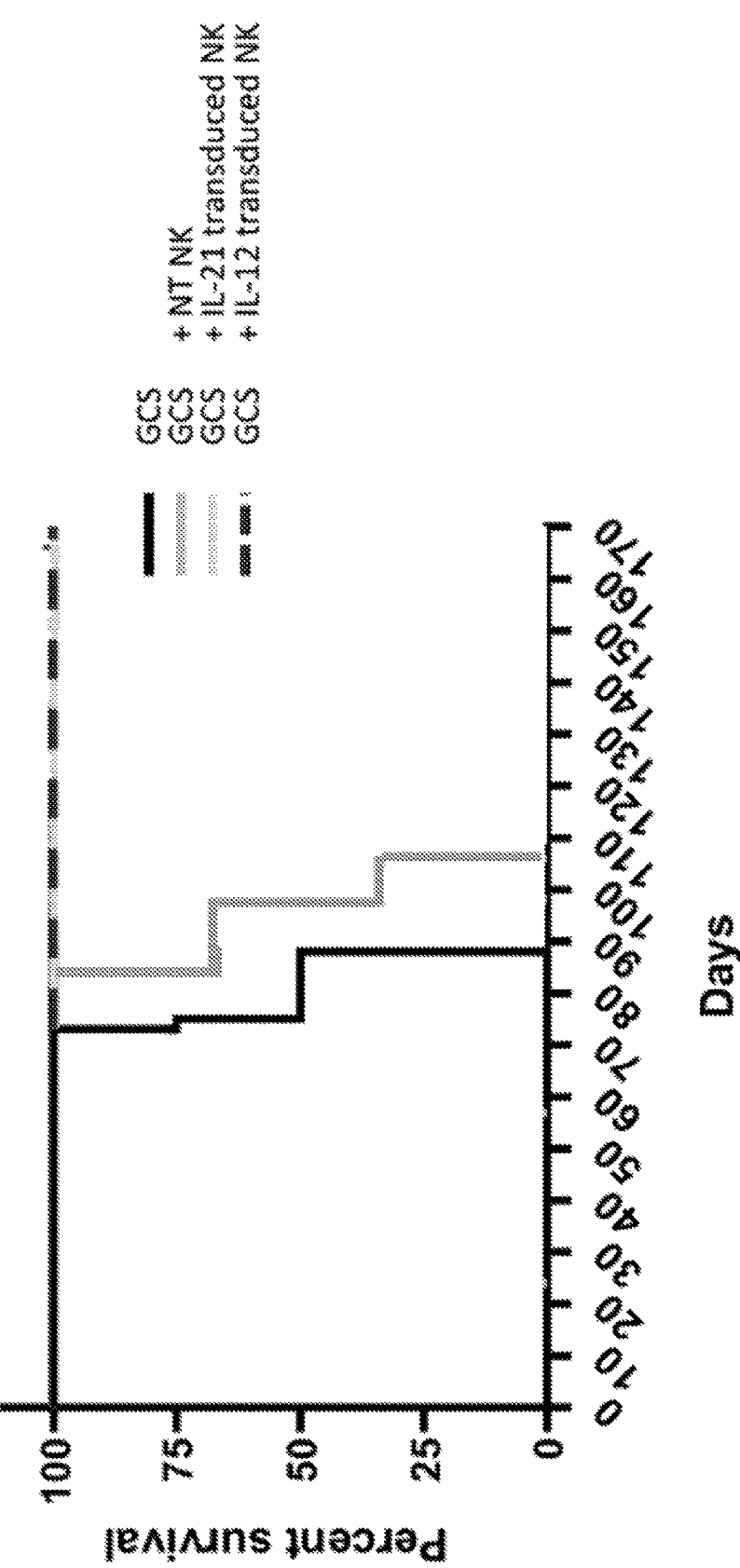

In vivo activity of NK cells against GBM was characterized. NOD/SCID/IL2Rγc null mice (n=5 per group) were stereotactically implanted with ffLuc+ patient-derived glioblastoma stem cell lines ($5\times10^5$) into the right forebrain of NSG mice. After 7 days and following confirmation by BLI imaging that the tumor was established, mice were treated intracranially with $1.0\times10^5$ NK cells as indicated for each experiment. Animals treated with IL-12-transduced or IL-21-transduced (secretable) cord blood NK cells had marked regression of tumor (tumor was no longer detectable by BLI imaging) with significantly improved overall survival compared to those treated with non-transduced (NT) NK cells (FIGS. 4A, 4B, and 4C).

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Publications

Ahmed et al. Clin Cancer Res 16(2): 474-485 (2010).
Austin-Ward and Villaseca, *Revista Medica de Chile,* 126(7):838-845, 1998.
Ausubel et al., *Current Protocols in Molecular Biology,* Greene Publishing Associates and John Wiley & Sons, NY, 1994. Brown et al., N. Engl J. Med. 375(26): 256-269. (2016).
Bukowski et al., *Clinical Cancer Res.,* 4(10):2337-2347, 1998.
Camacho et al. (2004) *J Clin Oncology* 22(145): Abstract No. 2505 (antibody CP-675206)
Cohen et al., *J Immunol.* 175:5799-5808, 2005. Chothia et al., 1988
Christodoulides et al., *Microbiology,* 144(Pt 11):3027-3037, 1998.
Davidson et al., *J. Immunother.,* 21(5):389-398, 1998.
Davila et al. *PLoS ONE* 8(4): e61338, 2013.

Heemskerk et al. *Hum Gene Ther.* 19:496-510, 2008.
Hellstrand et al., *Acta Oncologica,* 37(4):347-353, 1998.
Hollander, *Front. Immun.,* 3:3, 2012.
Hanibuchi et al., *Int. J. Cancer,* 78(4):480-485, 1998.
Hui and Hashimoto, *Infection Immun.,* 66(11):5329-5336, 1998.
Hurwitz et al. (1998) *Proc Natl Acad Sci USA* 95(17): 10067-10071
Johnson et al. *Blood* 114:535-46, 2009.
Jores et al., *PNAS U.S.A.* 87:9138, 1990.
Kabat et al., "Sequences of Proteins of Immunological Interest, US Dept. Health and Human Services, Public Health Service National Institutes of Health, 1991, 5th ed.
Leal, M., *Ann N Y Acad Sci* 1321, 41-54, 2014.
Lefranc et al., *Dev. Comp. Immunol.* 27:55, 2003.
Li, *Nat Biotechnol.* 23:349-354, 2005.
Mokyr et al. (1998) *Cancer Res* 58:5301-5304
O'Rourke et al. *Sci Transl Med* 9(399).
Parkhurst et al., *Clin Cancer Res.* 15: 169-180, 2009.
Pardoll, *Nat Rev Cancer,* 12(4): 252-64, 2012
Qin et al., *Proc. Natl. Acad. Sci. USA,* 95(24):14411-14416, 1998.
Sadelain et al., *Nat.Rev.Cancer* 2003; 3:35-45.
Sadelain et al., *Cancer Discov.* 3(4): 388-398, 2013.
Sambrook et al., *Molecular Cloning: A Laboratory Manual,* 3rd ed., Cold Spring Harbor Press, Cold Spring Harbor, N.Y. 2001.
Singh et al., *Cancer Research,* 68:2961-2971, 2008.
Singh et al., *Cancer Research,* 71:3516-3527, 2011.
Turtle et al., *Curr. Opin. Immunol.,* 24(5): 633-39, 2012.
Varela-Rohena et al. *Nat Med.* 14: 1390-1395, 2008.
Wu et al., *Cancer,* 18(2): 160-75, 2012.

Patents and Patent Applications

European patent application number EP2537416
U.S. Patent Publication No. 2005/0260186
U.S. Patent Publication No. 2006/0104968
U.S. Patent Publication No. 2002131960
U.S. Patent Publication No. 2013287748
U.S. Patent Publication No. 20130149337
U.S. Patent Application No. 2014/0294898
U.S. Patent Application No. 2014/022021
U.S. Patent Application No. 2011/0008369
U.S. Pat. No. 5,739,169
U.S. Pat. No. 5,801,005
U.S. Pat. No. 5,824,311
U.S. Pat. No. 5,830,880
U.S. Pat. No. 5,846,945
U.S. Pat. No. 5,844,905
U.S. Pat. No. 5,885,796
U.S. Pat. No. 6,207,156
U.S. Pat. No. 6,410,319
U.S. Pat. No. 6,451,995
U.S. Pat. No. 7,070,995
U.S. Pat. No. 7,109,304
U.S. Pat. No. 7,265,209
U.S. Pat. No. 7,354,762
U.S. Pat. No. 7,446,179
U.S. Pat. No. 7,446,190
U.S. Pat. No. 7,446,191
U.S. Pat. No. 8,008,449
U.S. Pat. No. 8,017,114
U.S. Pat. No. 8,119,129
U.S. Pat. No. 8,252,592
U.S. Pat. No. 8,324,353

41

U.S. Pat. No. 8,329,867
U.S. Pat. No. 8,339,645
U.S. Pat. No. 8,354,509
U.S. Pat. No. 8,398,282
U.S. Pat. No. 8,479,118
U.S. Pat. No. 8,735,553
WO 1995/001994
WO 1998/042752
WO 2000/14257
WO 2000/37504
WO 2001/014424
WO 2009/101611
WO 2009/114335
WO 2010/027827
WO 2011/066342
WO 2012/129514
WO 2013/071154
WO 2013/123061
WO 2013/126726
WO 2013/166321
WO 2014/031687
WO 2014/055668
WO 2015/016718

What is claimed is:

1. A composition comprising engineered natural killer (NK) cells, said engineered NK cells expressing one or more secretable heterologous interleukins (IL), wherein the secretable heterologous IL is selected from the group consisting of IL-21, IL-12, IL-2, IL-18, IL-7, and the p35 and p40 subunits of IL-12 artificially linked together with a linker, and wherein the NK cell expresses one or more chimeric antigen receptors (CAR) and/or T cell receptors (TCR) that target B7-H3, EGFRvIII, GD2, IL-13Ra2, CD5, CD70, or PRAME.

2. The composition of claim 1, wherein the IL is IL-12, IL-21, IL-18, or a combination thereof.

3. The composition of claim 1, wherein said IL is secreted, tethered, or membrane bound in the cell.

4. The composition of claim 1, wherein the one or more heterologous IL are expressed from a vector in the engineered NK cells and/or wherein the engineered NK cells are cultured in the presence of one or more IL.

5. The composition of claim 1, wherein the engineered NK cell comprises a suicide gene.

6. The composition of claim 1, wherein the engineered NK cell is reduced or inhibited in expression of one or more of endogenous genes selected from the group consisting of TDAG8, NKG2A, SIGLEC-7, LAG3, TIM3, CISH, FOXOl, TGFBR2, TIGIT, CD96, ADORA2, NR3C1, PD1, PDL-1, PDL-2, CD47, SIRPA, SHIP1, ADAM 17, RPS6, 4EBP1, CD25, CD40, IL21R, ICAM1, CD95, CD80, CD86, IL10R, CD5, CD7, and a combination thereof.

* * * * *